United States Patent [19]

Chowienczyk et al.

[11] Patent Number: 5,233,998

[45] Date of Patent: Aug. 10, 1993

[54] APPARATUS FOR MEASURING AIRWAY RESISTANCE

[75] Inventors: Philip J. Chowienczyk, London; Christopher P. Lawson, Rochester; Brian R. Cain, Chatham, all of England

[73] Assignee: Micro Medical Ltd., England

[21] Appl. No.: 940,777

[22] Filed: Sep. 4, 1992

Related U.S. Application Data

[63] Continuation of Ser. No. 580,124, Sep. 10, 1990, abandoned.

[30] Foreign Application Priority Data

Sep. 11, 1989 [GB] United Kingdom ............. 8920499.4

[51] Int. Cl.⁵ .......................................... A61B 5/08
[52] U.S. Cl. .................................. 128/720; 128/725
[58] Field of Search ............... 128/716, 718, 720, 725

[56] References Cited

U.S. PATENT DOCUMENTS

| | | | |
|---|---|---|---|
| 3,036,569 | 5/1962 | Clements | 128/720 |
| 3,410,264 | 11/1968 | Frederick | 128/720 |
| 3,621,833 | 11/1971 | Crane | 128/720 |
| 3,726,271 | 4/1973 | Mondshine | 128/718 |
| 3,857,385 | 12/1974 | Hampl | 128/720 |
| 4,082,088 | 4/1978 | Franetzki | 128/720 |
| 4,122,839 | 10/1978 | Franetzki | 128/720 |
| 4,220,161 | 9/1980 | Berlin | 128/720 |
| 4,259,967 | 4/1981 | Voreen | 128/720 |
| 4,558,710 | 12/1985 | Eichler | 128/720 |

OTHER PUBLICATIONS

*Effect of Valve Closure Time on the Determination of the Respiratory Resistance* by Flow Interruption, Bates et al, Medical Biological Engineering and Computing, 1985, vol. 25, pp. 136-140.

A multiplex cathode-ray-tube display w/ digital readout for a body plethysmograph, Reyohds et al, May 1973 Medical and Biological Engineering.

Estimation of Pulmonary Resistance by Repetitive Interruption of Airflow Clements et al, Journal of Clinical Investigation, vol. 38, No. 7, Jul. 1959, pp. 1262-1270.

*Primary Examiner*—William E. Kamm
*Assistant Examiner*—Robert L. Nasser, Jr.
*Attorney, Agent, or Firm*—Iandiorio & Dingman

[57] ABSTRACT

Apparatus for measuring airway resistance, which apparatus comprises a housing, a bore in the housing, a flow measuring device which is positioned in the bore and which is for measuring a flow of air through the bore caused by a person exhaling or inhaling, an interrupting valve device which is for interrupting the flow of air through the bore, a drive device for moving the interrupting valve device between a bore closing position and a bore opening position, and a pressure sensor device for sensing variations in pressure in the bore caused by the interrupting valve device closing and opening the bore and thus interrupting the flow of air through the bore, and the apparatus being such that the bore is of circular cross section, and the interrupting valve device is a non-circular eliptical plate member which is mounted in the bore for pivotal movement by the drive device between the bore closing position and the bore opening position and which extends at an acute angle to the bore in the bore closing position.

7 Claims, 3 Drawing Sheets

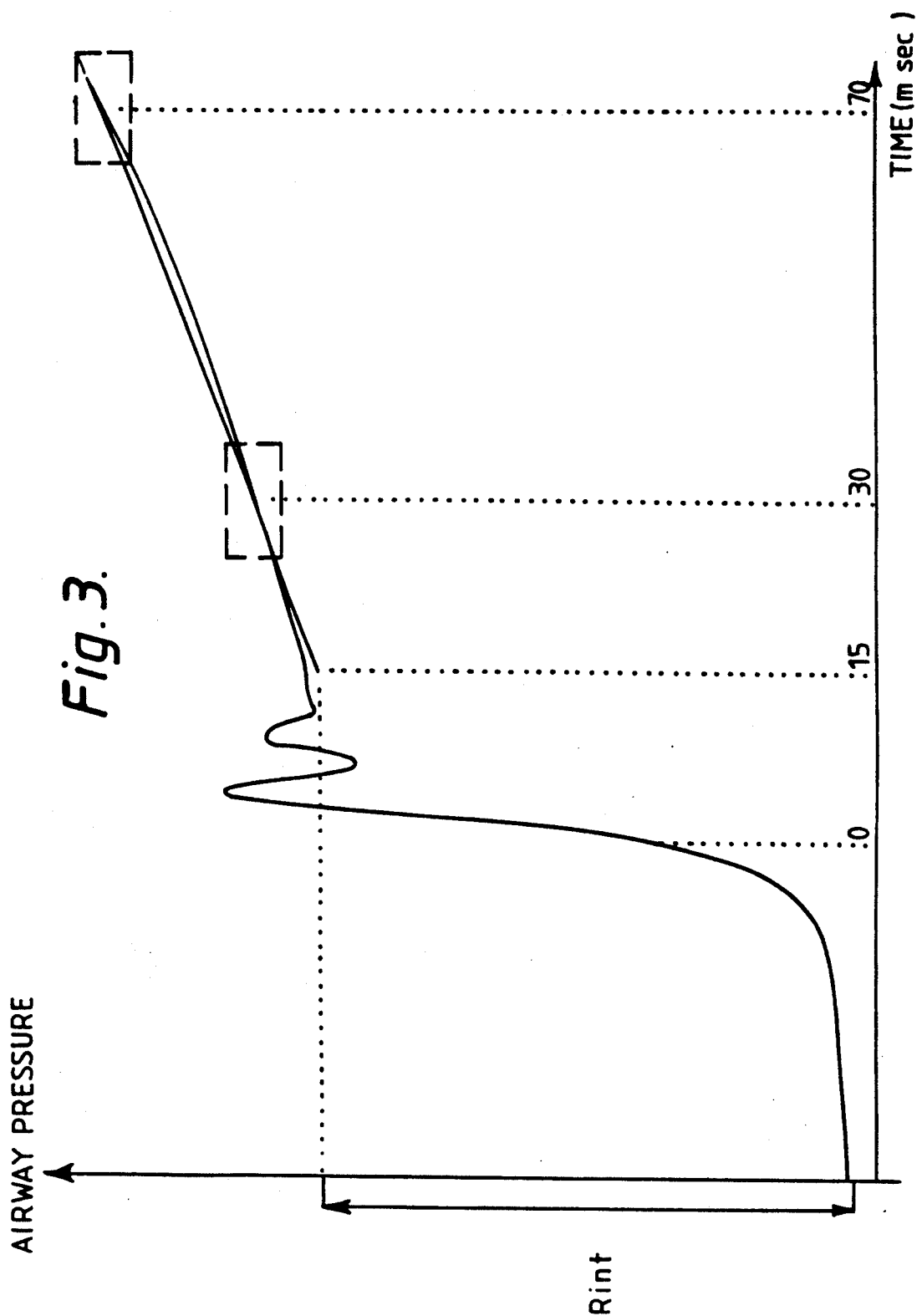

APPARATUS FOR MEASURING AIRWAY RESISTANCE

This is a continuation of application Ser. No. 07/580,124, filed Sep. 10, 1990 now abandoned.

This invention relates to apparatus for measuring airway resistance and, more especially, this invention relates to apparatus for measuring airway resistance in patients using an interrupter method.

In patients, it is often necessary to assess their airway caliber, or changes in their airway caliber following therapeutic intervention such for example as spirometry. Conventional tests and apparatus for assessing the airway calibre or the changes in the airway caliber require a relatively high degree of patient co-operation. This precludes the conventional tests and apparatus in an important group of patients, namely neonates, pre-school children, the critically ill, comatose patients, and some geriatric patients.

A known but non-conventional and hitherto unexploited method of assessing airway caliber and changes in airway caliber is known as the airway occlusion or interrupter method. This interrupter method has the potential to provide a measurement of airway caliber which requires minimal patient co-operation. The principle of operation is that during transient interruption of airflow, alveolar pressure will equilibrate rapidly with pressure at the mouth. Measurement of mouth pressure immediately post occlusion will therefore give alveolar pressure. Provided occlusion is sufficiently rapid, alveolar pressure immediately post occlusion will approximate alveolar pressure immediately prior to occlusion. The ratio of this pressure to flow rate at the time of occlusion is the airway resistance as determined by the interrupter method. Airway resistance is related to airway caliber. The interrupter method has not been widely used, partly because equipment required is technically difficult to produce and partly because of theoretical reservations regarding the validity of the interrupter method. There has been little experimental data published to refute or support the interrupter method. Recent theoretical analyses suggest that the interrupter method is essentially valid, although upper airway compliance may cause the airway resistance as determined by the interrupter method to under estimate the true value of the airway resistance.

Since the interrupter method has the facility to be used with the above mentioned precluded important group of patients, it is an aim of the present invention to provide apparatus for measuring airway resistance based on the interrupter method.

Accordingly, this invention provides apparatus for measuring airway resistance, which apparatus comprises a housing, a bore in the housing, flow measuring means which is positioned in the bore and which is for measuring a flow of air through the bore caused by a person exhaling or inhaling, interrupting valve means which is for interrupting the flow of air through the bore, drive means for moving the interrupting valve means between a bore closing position and a bore opening position, and pressure sensor means for sensing variations in pressure in the bore caused by the interrupting valve means closing and opening the bore and thus interrupting the flow of air through the bore, and the apparatus being such that the bore is of a circular cross section, and the interrupting valve means is a non-circular eliptical plate member which is mounted in the bore for pivotal movement by the drive means between the bore closing position and the bore opening position and which extends at an acute angle to the bore in the bore closing position.

The apparatus of the present invention may be particularly simple to use, may require no co-operation by the patients, may be portable, and may provide a direct instantaneous measurement of airway caliber.

Usually, the pressure sensor means, the flow resistive means and the interrupting valve means will be connected together in series in close proximity to each other, with the flow measuring means being positioned between the interrupting valve means and the pressure sensor means.

The pressure sensor means may be a piezo-electric pressure sensitive element.

The flow measuring means is preferably a flow resistive means, for example a stainless steel gauze.

The interrupting means may include a drive motor. Preferably, the drive motor is a servo motor.

The apparatus of the invention may include computer means. The computer means may comprise a microcomputer, an analog to digital converter, display means, a graphics printer, and a miniature keyboard. The microcomputer is preferably a single chip microcomputer.

The apparatus of the invention may include switch means for reversing the polarity of an obtained pressure signal and hence a flow signal in order to allow the apparatus to measure airway resistance on inspiration or expiration.

An embodiment of the invention will now be described solely by way of example and with reference to the accompanying drawings in which:

FIG. 3 is an analysis of airway pressure against time.

Figure 1:
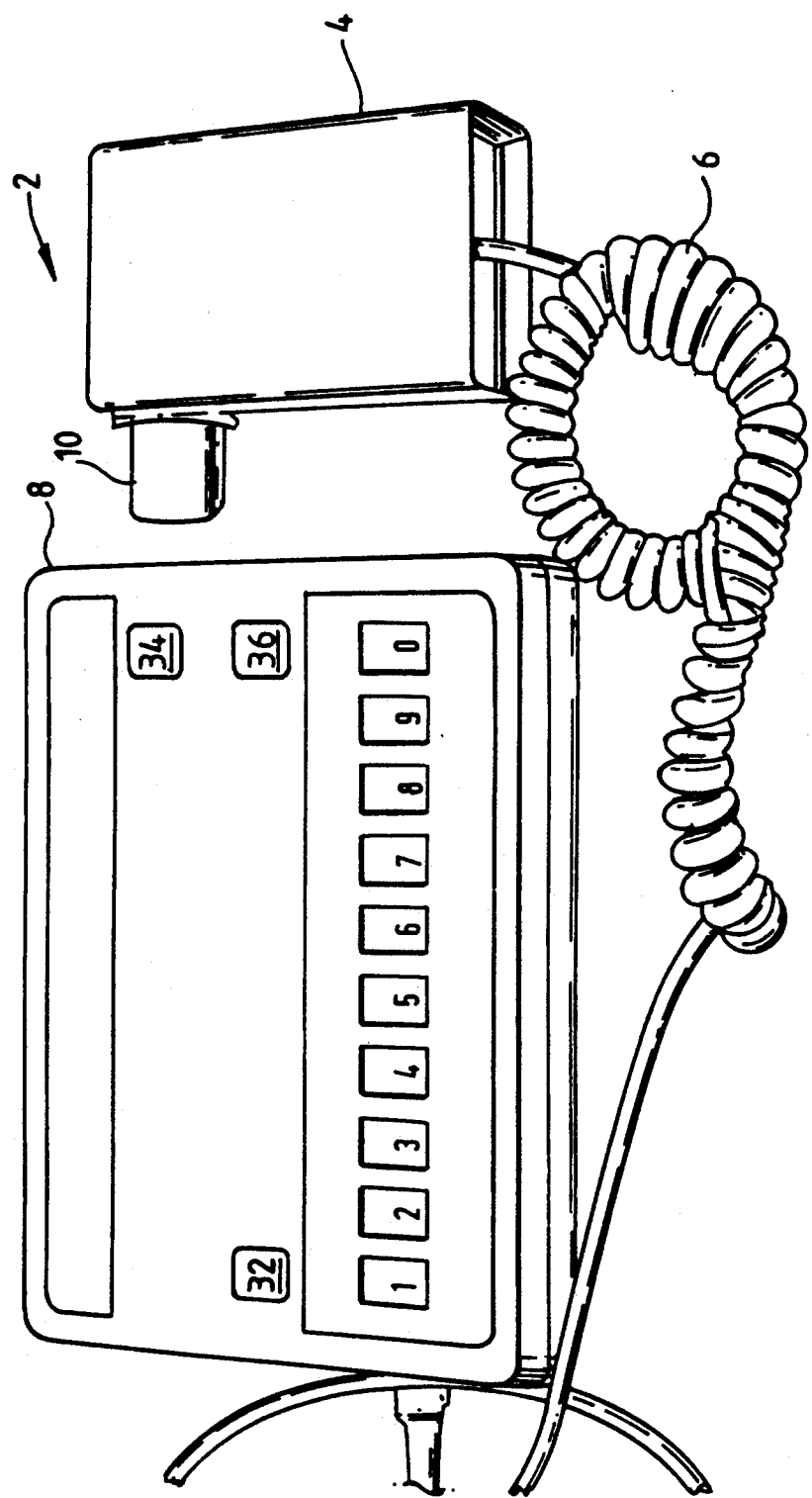
FIG. 1 shows apparatus for measuring airway resistance.

Referring to FIG. 1, there is shown apparatus 2 for measuring airway pressure using an interrupter method. The apparatus 2 comprises a transducer unit 4 connected by a cable 6 to computer means in the form of a custom built miniature computer unit 8. The transducer unit 4 connects directly to a patient's airway either via a face mask (not shown) or a mouthpiece 10.

Figure 2:
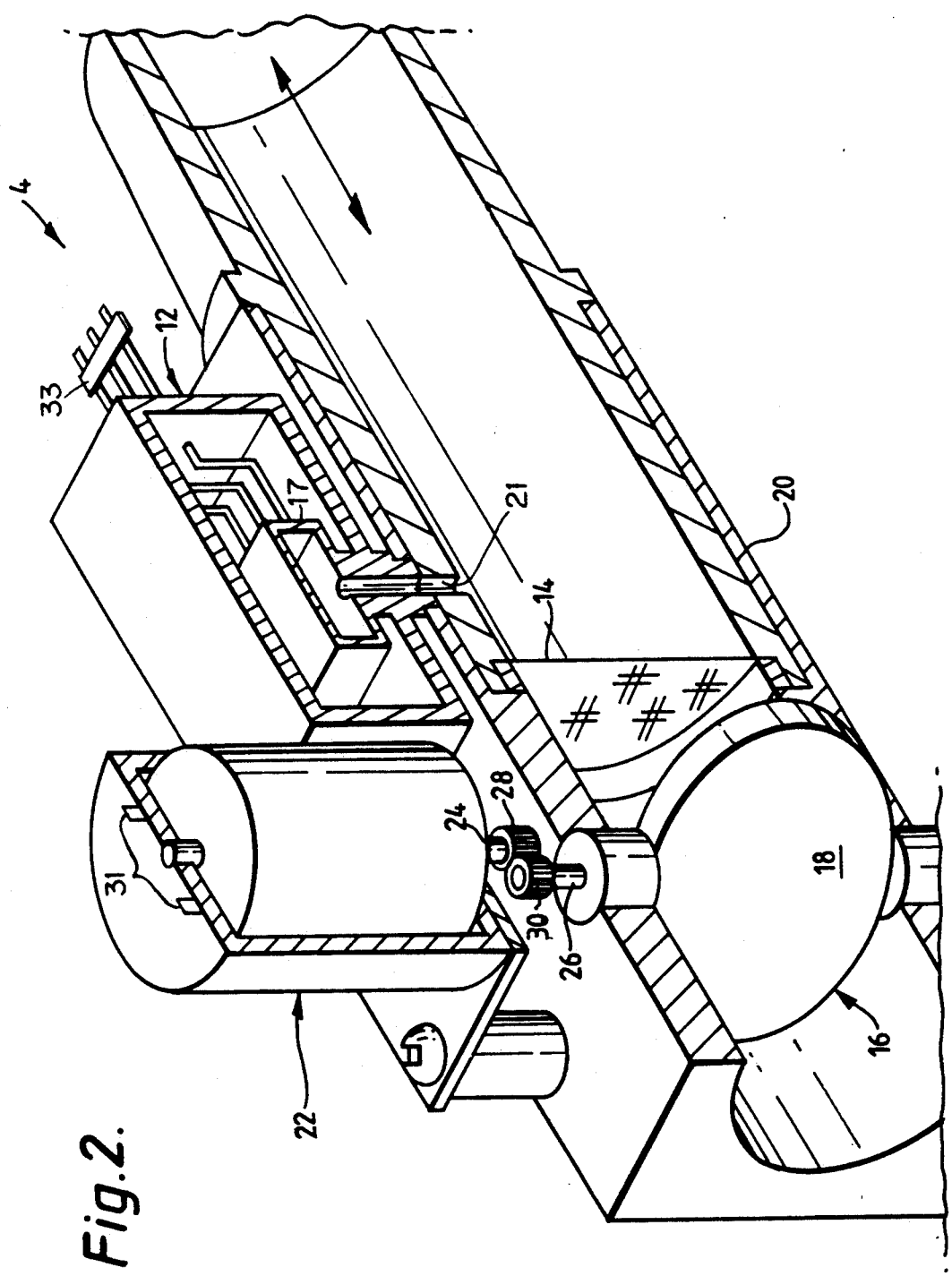
FIG. 2 shows somewhat schematically a cross section through part of the apparatus shown in FIG. 1.

The transducer unit 4 is designed to facilitate accurate measurement of the airway resistance as determined by the interrupter method. The transducer unit 4 does this by achieving rapid airway occlusion and high fidelity recording of the pressure transient. The transducer unit 4 comprises a series combination of pressure sensor means in the form of a pressure sensor 12, flow measuring means in the form of a flow resistive element 14, and an interrupting valve 16 which may be regarded as an occluding valve. The pressure sensor 12, the flow resistive element 14 and the interrupting valve 16 are connected together in close proximity as shown in FIG. 2. The pressure sensor 12 includes a piezo-electric pressure sensitive element located in a housing 17. The pressure sensor 12 is connected to the the bore or lumen of a tube 20 by a passageway 21 which gives a dead space of less than 0.2 mls. This ensures accurate recording of pressure transients at frequencies up to 500 Hz.

Interposition of the flow resistive element 14 between the pressure sensor 12 and the interrupting valve 16 generates a pressure dependent on flow. When the interrupting valve 16 is open, airway flow can be measured in terms of recorded pressure.

The interrupting valve 16 includes a lightweight non-circular elliptical plate 18 which is driven to occlude the lumen of a tube 20. Forces on the occluding plate 18 generated as a result of airflow through the interrupting valve 16 are balanced. Therefore only minimal force is required to move the plate 18. The use of an elliptical plate 18 rather than a circular plate 18 eliminates frictional forces between the surfaces of the plate 18 and the tube lumen when the interrupting valve 16 is closed. This again reduces the force required to drive the interrupting valve 16. A rapid speed of occlusion is achieved which is approximately 4 msec. The occluding valve 16 is lightweight, requires minimum electrical power and is unobtrusive in use. The interrupting valve 18 is driven by drive means in the form of a servomotor 22 which drives the plate 18 via shafts 24, 26 and cogs 28, 30.

Control signals to the interrupting valve 16 and the analog signal from the pressure transducer 12 are passed to the computer unit 8. The computer unit 8 is a dedicated computer unit comprising a signal chip microcomputer, an analog to digital converter, a liquid crystal display, a graphics printer and a miniature keyboard. The computer 8 connects to terminals 31 of the servo motor 22.

The apparatus 2 operates as follows. With the interrupting valve 16 open, pressure and hence flow are continually monitored. When the flow reaches a predetermined value, which is usually 0.5 l/s, the interrupting valve 16 is actuated. For the next 100 msec pressure values are stored in a memory part of the computer unit 8 at intervals of 1 msec. Approximately 5 msec after the valve is actuated, complete airway occlusion is achieved. The interrupting valve 18 is held in the closed position for a further 100 msec. This period of airway occlusion is virtually imperceptible to the patient. The interrupting valve 16 is then opened and the stored pressure transient obtained as a result of the closing and opening of the interrupting valve 18 is analysed to compute the airway resistance as determined by the interrupter technique, see FIG. 3. In FIG. 3, the time ($t_0$) of the complete airway occlusion is defined as that at which the pressure signal reaches 25% of the difference between the maximum value of the first clearly defined peak of pressure oscillations and the baseline value. The signal is then averaged over two 10 msec time periods. The first time period is centred on a time ($t_0$)+30 msec, and the second time period is centred on a time ($t_0$)+70 msec. These two average values are used to back extrapolate the pressure transient to a time ($t_0$)+15 msec. The difference between this and the baseline pressure immediately prior to interruption is taken as the alveolar pressure at the time of interruption. The airway resistance as determined by the interrupter technique is taken as the ratio of this pressure to flow at the time of the interruption.

A switch 33 allows reversal of the polarity of the pressure signal (and hence the flow signal) and thus allows measurements to be made in inspiration or expiration as desired.

It is to be appreciated that the embodiment of the invention described above with reference to the accompanying drawings has been given by way of example only and that modifications may be effected. Thus, for example, a different type of pressure sensor 12 and a different type of interrupting valve 16 to those illustrated may be employed. The flow resistive element 14 may be of a shape other than the illustrated disc shape. The flow resistive element 14 may be a stainless steel gauze which causes a small pressure drop across the gauze as a patient breathes during use of the apparatus 2. Flow resistive elements 14 other than stainless steel gauze ones may be employed. Also, other types of flow measuring means may be employed since using a flow resistive means is just a presently preferred way of measuring air flow which enables the use of a single pressure transducer for measuring the airway flow when the interrupting valve 16 is open and also for measuring air pressure at a patient's mouth when the interrupting vale 16 is closed. The computer unit 8 is shown as having a paper feed button 32, a cancel button 34, an enter button 36 and a number of buttons 1–0 as shown. The numbers buttons 1–0 give a flow threshold which causes the interrupting valve 16 to move to its closed position when the patient's breath reaches the set flow threshold. The computer unit 8 may be modified, for example to reduce the number of buttons 1–0 thereby to reduce the number of selectable flow thresholds.

What is claimed is:

1. Apparatus for measuring airway resistance, which apparatus comprises a housing, a bore in the housing, flow measuring means which is positioned in the bore and which is for measuring a flow of air through the bore caused by a person exhaling or inhaling, interrupting valve means which is for interrupting the flow of air through the bore, drive means for moving the interrupting valve means between a bore closing position and a bore opening position, and pressure sensor means for sensing variations in the pressure in the bore caused by the interrupting valve means closing and opening the bore and thus interrupting the flow if air through the bore, and the apparatus being such that the bore is of a circular cross section, and the interrupting valve means is a non-circular elliptical plate member which is mounted in the bore for pivotal movement by the drive means between the bore closing position and the bore opening position and which extends at an acute angle to the bore in the bore closing position.

2. Apparatus according to claim 1 in which the pressure sensor means, the flow measuring means and the interrupting valve means are connected together in series in close proximity to each other, with the flow measuring means being positioned between the interrupting valve means and the pressure sensor means.

3. Apparatus according to claim 1 in which the pressure sensor means is a piezo-electric pressure sensitive element.

4. Apparatus according to claim 1 in which the flow measuring means includes flow resistive means for measuring a flow of air through said bore.

5. Apparatus according to claim 1 in which the interrupting means includes a drive motor.

6. Apparatus according to claim 1 and including switch means for reversing the polarity of an obtained pressure signal and hence a flow signal in order to allow the apparatus to measure airway resistance on inspiration or expiration.

7. Apparatus for measuring airway resistance, comprising: a housing, a bore in the housing, flow measuring means which is positioned in the bore and which is for measuring a flow of air through the bore caused by a person exhaling or inhaling, interrupting valve means which is for interrupting the flow of air through the bore, drive means for moving the interrupting valve means between a bore closing position and a bore opening position, and pressure sensor means for sensing variations in the pressure in the bore caused by the interrupting valve means closing and opening the bore and thus interrupting the flow of air through the bore, and the apparatus being such that the bore is of a circular cross section, the interrupting valve means is a non-circular elliptical plate member, pivot means for pivotally mounting said plate member in the bore, the drive means is a servomotor which is connected to the pivot means and which drives said pivotally mounted plate member through the pivot means between the bore closing position and the bore opening position, and the non-circular elliptical plate member is such that it extends at an acute angle to the bore in the bore closing position.

* * * * *